(12) United States Patent
Nierenberg et al.

(10) Patent No.: US 11,803,753 B1
(45) Date of Patent: *Oct. 31, 2023

(54) APPARATUS AND PRODUCT OF MANUFACTURE FOR GENERATING A PROBABILITY VALUE FOR AN EVENT

(71) Applicant: Persyst Development Corporation, Solana Beach, CA (US)

(72) Inventors: Nicolas Nierenberg, La Jolla, CA (US); Scott B. Wilson, Del Mar, CA (US)

(73) Assignee: Persyst Development Corporation, Solana Beach, CA (US)

( * ) Notice: Subject to any disclaimer, the term of this patent is extended or adjusted under 35 U.S.C. 154(b) by 461 days.

This patent is subject to a terminal disclaimer.

(21) Appl. No.: 17/175,635

(22) Filed: Feb. 13, 2021

Related U.S. Application Data

(63) Continuation of application No. 16/101,485, filed on Aug. 12, 2018, now Pat. No. 10,929,753, which is a continuation of application No. 14/222,655, filed on Mar. 23, 2014, now abandoned.

(60) Provisional application No. 61/929,120, filed on Jan. 20, 2014.

(51) Int. Cl.
*G06N 3/08* (2023.01)
(52) U.S. Cl.
CPC ..................... *G06N 3/08* (2013.01)
(58) Field of Classification Search
None
See application file for complete search history.

(56) References Cited

U.S. PATENT DOCUMENTS

| | | |
|---|---|---|
| RE30,502 E | 2/1981 | Lencioni, Jr. |
| 4,550,736 A | 11/1985 | Broughton et al. |
| 4,644,956 A | 2/1987 | Morgenstern |
| 4,709,702 A | 12/1987 | Sherwin |
| 4,936,306 A | 6/1990 | Doty |
| 4,967,038 A | 10/1990 | Gevins et al. |
| 5,038,782 A | 8/1991 | Gevins et al. |
| 5,230,344 A | 7/1993 | Ozdamar et al. |
| 5,230,346 A | 7/1993 | Leuchter et al. |
| 5,305,746 A | 4/1994 | Fendrock |
| 5,309,909 A | 5/1994 | Gadsby et al. |
| 5,626,145 A | 5/1997 | Clapp et al. |
| 5,730,146 A | 3/1998 | Itil et al. |

(Continued)

FOREIGN PATENT DOCUMENTS

| | | |
|---|---|---|
| WO | WO2000039337 | 7/2000 |
| WO | WO2100088227 | 7/2011 |

OTHER PUBLICATIONS

Technical Committee of the International Organization of Securities Commissions, The Role of Credit Rating Agencies in Structured Finance Markets, 2008, pp. 1-36 (Year: 2008).*

(Continued)

*Primary Examiner* — Wilbert L Starks
(74) *Attorney, Agent, or Firm* — Clause Eight; Michael Catania

(57) ABSTRACT

A method and system for generating a probability value for an event. The system includes a source for generating a plurality of digital input signals, a processor connected to the source to receive the plurality of digital input signals from the source, and a display connected to the processor for displaying a final output. Preferably, the method further includes validating the probability value.

5 Claims, 15 Drawing Sheets

(56) References Cited

U.S. PATENT DOCUMENTS

| | | | |
|---|---|---|---|
| 5,846,208 | A | 12/1998 | Pichlmayr et al. |
| 6,224,549 | B1 | 5/2001 | Drongelen |
| 6,334,856 | B1 | 1/2002 | Allen et al. |
| 6,493,576 | B1 | 12/2002 | Dankwart-Eder |
| 6,591,132 | B2 | 7/2003 | Gotman et al. |
| 6,735,467 | B2 | 5/2004 | Wilson |
| 6,931,274 | B2 | 8/2005 | Williams |
| 7,286,871 | B2 | 10/2007 | Cohen |
| 7,754,190 | B2 | 7/2010 | Suffin |
| 7,809,433 | B2 | 10/2010 | Keenan |
| 7,904,144 | B2 | 3/2011 | Causevic et al. |
| 7,941,201 | B2 | 5/2011 | Chiou et al. |
| 8,112,141 | B2 | 2/2012 | Wilson et al. |
| 8,155,736 | B2 | 4/2012 | Sullivan et al. |
| 8,185,183 | B1 | 5/2012 | Wilson et al. |
| 8,271,065 | B1 | 9/2012 | Wilson et al. |
| 8,428,681 | B2 | 4/2013 | Wilson et al. |
| 8,447,407 | B2 | 5/2013 | Talathi et al. |
| 8,538,502 | B1 | 9/2013 | Wilson et al. |
| 8,666,484 | B2 | 3/2014 | Nierenberg et al. |
| 8,694,070 | B2 | 4/2014 | Wilson |
| 8,972,001 | B2 | 3/2015 | Nierenberg et al. |
| 9,055,927 | B2 | 6/2015 | Wilson et al. |
| 9,232,922 | B2 | 1/2016 | Wilson et al. |
| 10,022,291 | B2 | 7/2018 | Wilson et al. |
| 10,105,091 | B2 | 10/2018 | Papay et al. |
| 2002/0082551 | A1 | 6/2002 | Ennen et al. |
| 2002/0099306 | A1 | 7/2002 | Shaw et al. |
| 2003/0144601 | A1 | 7/2003 | Prichep |
| 2004/0059241 | A1 | 3/2004 | Suffin |
| 2004/0152957 | A1 | 8/2004 | Stivoric et al. |
| 2005/0059874 | A1 | 3/2005 | Fuchs et al. |
| 2005/0144042 | A1 | 6/2005 | Joffe et al. |
| 2006/0058606 | A1 | 3/2006 | Davis et al. |
| 2007/0135727 | A1 | 6/2007 | Virtanen et al. |
| 2007/0167858 | A1 | 7/2007 | Virtanen et al. |
| 2008/0027515 | A1 | 1/2008 | Harris et al. |
| 2008/0234973 | A1 | 9/2008 | Ali |
| 2008/0262335 | A1 | 10/2008 | Sun et al. |
| 2008/0269630 | A1 | 10/2008 | Denison et al. |
| 2009/0062680 | A1 | 3/2009 | Sandford |
| 2009/0247895 | A1 | 10/2009 | Morikawa et al. |
| 2010/0098289 | A1 | 4/2010 | Tognoli et al. |
| 2011/0015503 | A1 | 1/2011 | Joffe et al. |
| 2011/0178421 | A1 | 7/2011 | Schultz |
| 2011/0224569 | A1 | 9/2011 | Isenhart et al. |
| 2012/0277618 | A1 | 11/2012 | Giftakis et al. |
| 2013/0261490 | A1 | 10/2013 | Truccolo et al. |
| 2015/0112223 | A1 | 4/2015 | Nierenberg et al. |
| 2015/0351654 | A1 | 12/2015 | Kilsgaard et al. |
| 2017/0061217 | A1 | 3/2017 | Cha et al. |

OTHER PUBLICATIONS

Kappenman, et al., The Effects of Electrode Impedance on Data Quality and Statistical Significance in ERP Recordings, Psychophysiology, 2010, 47(5), pp. 888-904 (Year: 2010).*

Kamath, A New Approach to Detect Epileptic Seizures in Electroencephalograms Using Teager Energy, ISRN Biomedical Engineering, 2013, pp. 1-14 (Year: 2013).*

* cited by examiner

APPARATUS AND PRODUCT OF MANUFACTURE FOR GENERATING A PROBABILITY VALUE FOR AN EVENT

CROSS REFERENCES TO RELATED APPLICATIONS

The Present Application is a continuation of U.S. patent application Ser. No. 16/101,485, filed on Aug. 12, 2018, which is a continuation of U.S. patent application Ser. No. 14/222,655, filed on Mar. 23, 2014, now abandoned, which claims priority to U.S. Provisional Patent Application No. 61/929,120, filed on Jan. 20, 2014, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to a method and system for generating a probability value. More specifically, the present invention relates to a method and system for training a neural network for generating a probability value.

Description of the Related Art

Artificial neural networks are computational models capable of machine learning and pattern recognition. The artificial neural network generally is interconnected neurons that compute values from inputs by feeding data through the artificial neural network. Artificial neural networks have application in numerous areas including voice recognition, medical diagnosis, finance, trading, facial recognition, chemistry, game playing, decision making, robotics, and the like.

General definitions for terms utilized in the pertinent art are set forth below.

Boolean algebra is the subarea of algebra in which the values of the variables are the truth values true and false, usually denoted 1 and 0 respectively.

A Boolean network (BN) is a mathematical model of biological systems based on Boolean logic. The BN has a network structure consisting of nodes that correspond to genes or proteins. Each node in a BN takes a value of 1 or 0, meaning that the gene is or is not expressed.

Fuzzy logic is a form of many-valued logic; it deals with reasoning that is approximate rather than fixed and exact. Compared to traditional binary sets (where variables may take on true or false values) fuzzy logic variables may have a truth value that ranges in degree between 0 and 1. Fuzzy logic has been extended to handle the concept of partial truth, where the truth value may range between completely true and completely false. Furthermore, when linguistic variables are used, these degrees may be managed by specific functions. Irrationality can be described in terms of what is known as the "fuzzjective".

Multilayer perceptron ("MLP") is a feedforward artificial neural network model that maps sets of input data onto a set of appropriate outputs. An MLP consists of multiple layers of nodes in a directed graph, with each layer fully connected to the next one. Except for the input nodes, each node is a neuron (or processing element) with a nonlinear activation function.

Neural network ("NN") is an interconnected group of natural or artificial neurons that uses a mathematical or computational model for information processing based on a connectionistic approach to computation. In more practical terms neural networks are non-linear statistical data modeling or decision making tools. They can be used to model complex relationships between inputs and outputs or to find patterns in data.

Perceptron is a simple model of an artificial neuron which can predict boolean events after having been trained on past events. The perceptron is specified by the number of inputs N, and the weights connecting the inputs to the output node. The weights are the parameters which must be either set by hand or learned by a learning algorithm.

ROC curve (receiver operating characteristic) is a graphical plot of test sensitivity as the y coordinate versus its 1 minus specificity or false positive rate (FPR), as the x coordinate. The ROC curve is an effective method of evaluating the performance of diagnostic tests.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders, monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded. Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert. Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4 Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

The following definitions are used herein.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a nonmetallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right "Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy.

"Filtering" refers to a process that removes unwanted frequencies from a signal.

"Filters" are devices that alter the frequency composition of the signal.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

"Periodicity" refers to the distribution of patterns or elements in time (e.g., the appearance of a particular EEG activity at more or less regular intervals). The activity may be generalized, focal or lateralized.

"Sampling" or the term "sampling the signal" refers to reducing a continuous signal to a discrete signal. A digital signal is a sampled signal; obtained by sampling the analogue signal at discrete points in time.

The term "sampling interval" is the time between successive samples; these points are usually evenly spaced in time.

The term "sampling rate" refers to the frequency expressed in Hertz (Hz) at which the analogue-to-digital converter (ADC) samples the input analogue signal.

The term "Signal to Noise Ratio" (SNR) refers to a measurement of the amplitude of variance of the signal relative to the variance of the noise.

An EEG epoch is an amplitude of a EEG signal as a function of time and frequency.

Thus, there is a need for improving training of neural networks.

BRIEF SUMMARY OF THE INVENTION

The present invention provides a solution to the shortcomings of the prior art. The present invention provides a method and system for training a neural network.

One aspect of the present invention is a system for generating a probability value for an event. The system includes a source for generating a plurality of digital input signals, a processor connected to the source to receive the plurality of digital input signals from the source, and a display connected to the processor for displaying a final output.

Preferably, the processor is configured to submit the plurality of digital input signals to a recognition algorithm to generate a raw score, to calibrate the raw score to generate a probability value that an event has occurred, and to generate a display of the probability value versus time. The processor is further configured to validate the probability value.

Preferably, the system further includes that the plurality of digital input signals comprises at least one of a value for a fraudulent credit card transaction, a value for a monthly salary income for the loan applicant, a value for monthly rental income for the loan applicant, a value of a collateral for the loan, a value for a monthly car payment for the loan applicant, a value of a number of years employed for the loan applicant.

Another aspect of the present invention is a method for generating a probability value for an event. The method includes generating a plurality of digital input signals from a machine comprising a source, a processor and a display, submitting the plurality of digital input signals to a recognition algorithm to generate a raw score, calibrating the raw score to generate a probability value that an event will occur, and generating a graph of the probability value versus time.

Preferably, the method further includes validating the probability value.

Yet another aspect of the present invention is a system for validating a seizure probability for an EEG. The system includes a plurality of electrodes for generating a plurality of EEG signals, a processor connected to the plurality of electrodes to generate an EEG recording from the plurality of EEG signals, and a display connected to the processor for displaying a seizure detection probability.

Preferably, the processor is configured to submit the EEG recording to a neural network to generate a raw score, to calibrate the raw score to generate a probability value for a seizure, and to generate a graph of the probability value versus time. The processor is also preferably configured to validate the probability value.

Yet another aspect of the present invention is a method for validating a seizure probability for an EEG. The method includes generating a plurality a plurality of EEG signals, generating an EEG recording from the plurality of EEG signals, submitting the EEG recording to a neural network to generate a raw score, calibrating the raw score to generate a probability value that a seizure has occurred, and generating a graph of the probability value versus time.

Preferably, the method further includes validating the probability value.

Yet another aspect of the present invention is a method for generating a probability value for an event. The method includes generating a plurality of training set inputs from a machine comprising a source, a processor and a user-interface, submitting the plurality of training set inputs to a recognition algorithm to generate a raw score, calibrating the raw score to generate a probability value that an event will occur, validating a set to test, and generating probability values against data submitted for analysis.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
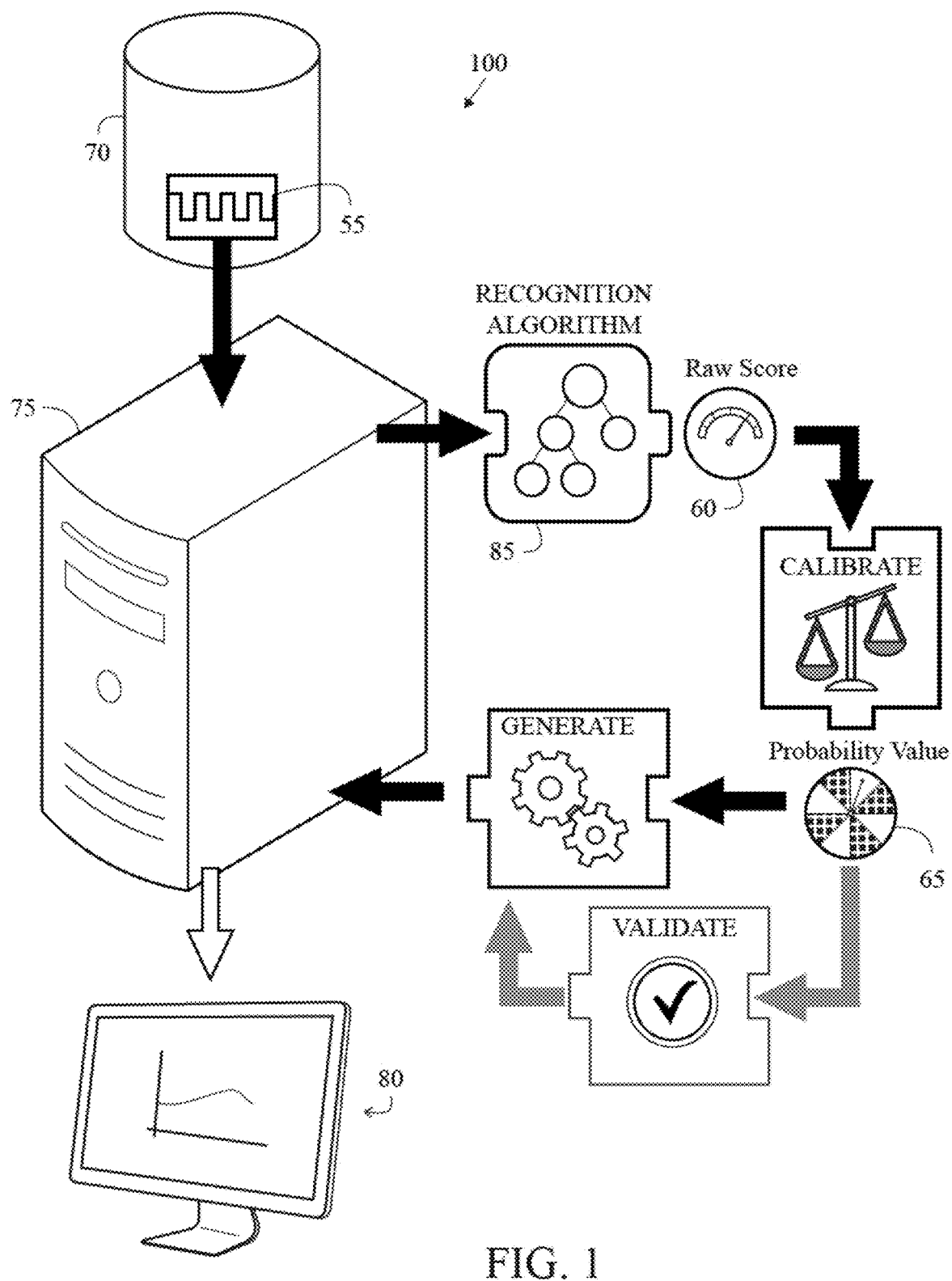
FIG. 1 is a block diagram of a system for generating a probability value for an event.
Figure 1A:
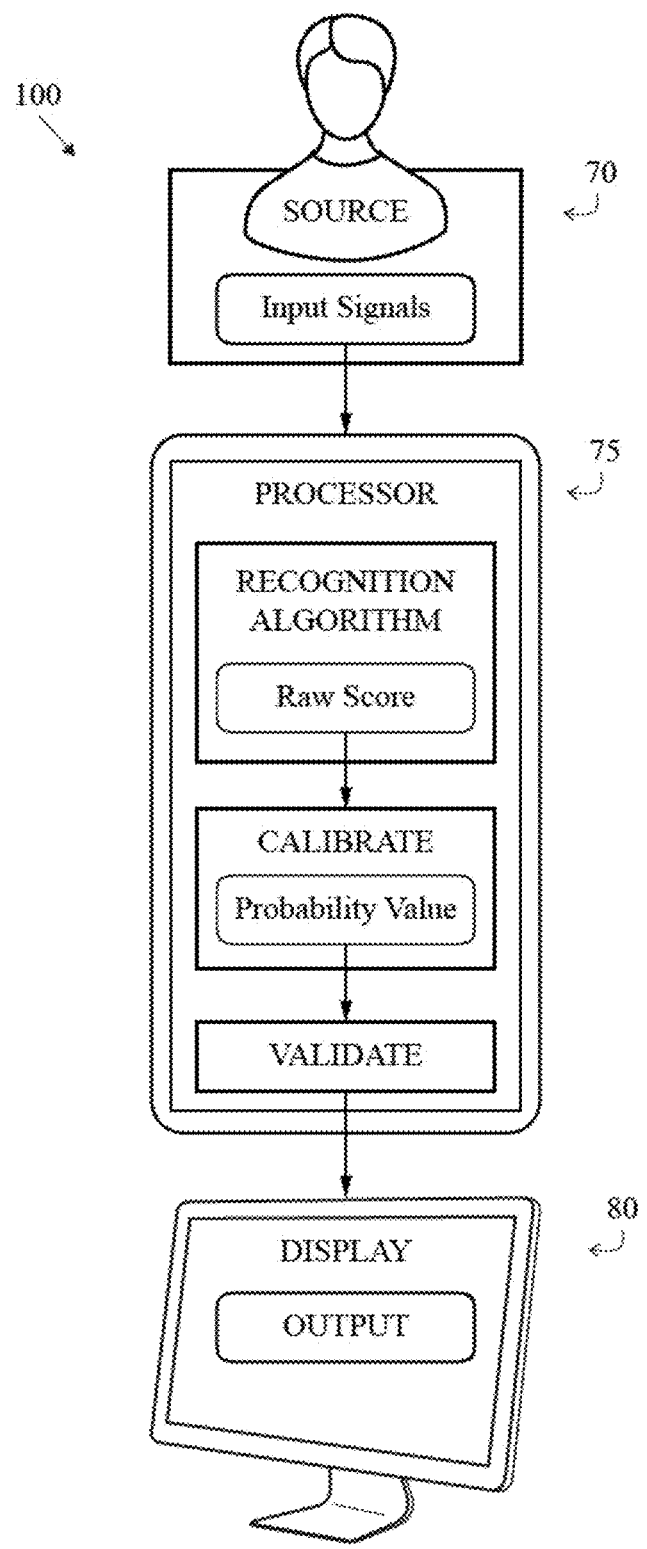
FIG. 1A is a block diagram of a system for generating a probability value for an event.

As shown in FIGS. 1 and 1A, a system for generating a probability value is generally designated 100. The system 100 preferably comprises a source 70, a processor 75, and a display 80. The source 70 generates digital input signals, which are received by a processor 75 that is connected to the source 70. The processor 75 is configured to submit the digital input signals to a recognition algorithm 85 to generate a raw score 60. The processor 75 is also configured to calibrate the raw score 60 to generate a probability value 65 that an event has occurred and then to generate a display of the probability value 65 versus time. Further, the processor 75 is configured to validate the probability value 65. The processor 75 is also connected to a display 80 for displaying a final output.

Figure 2:
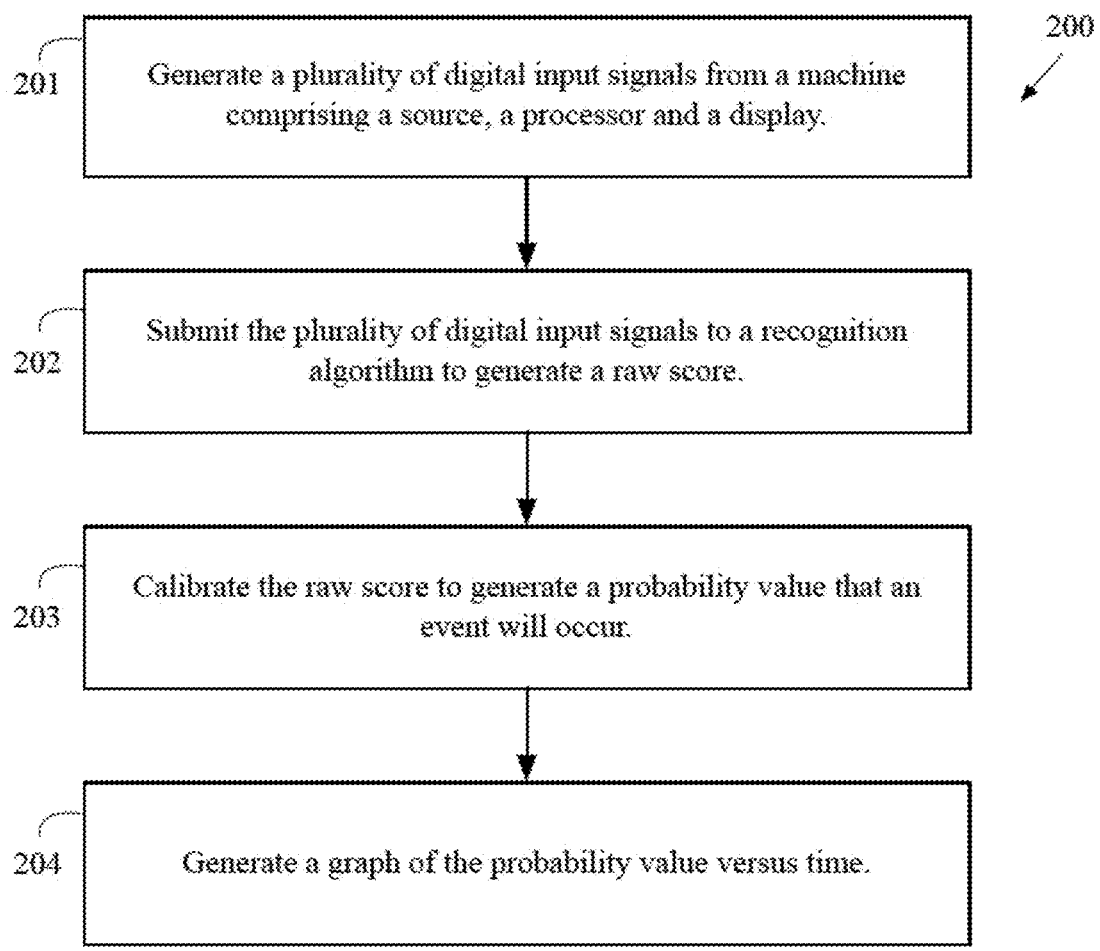
FIG. 2 is a flow chart of a method for generating a probability value for an event.

A general method 200 for generating a probability value is illustrated in the flow chart of FIG. 2. At block 201, a plurality of digital input signals is generated from a machine comprising a source, a processor and a display. At block 202, the plurality of digital input signals is submitted to a recognition algorithm to generate a raw score. At block 203, a raw score is calibrated to generate a probability value that an event will occur. At block 204, a graph of the probability value versus time is generated.

Figure 3:
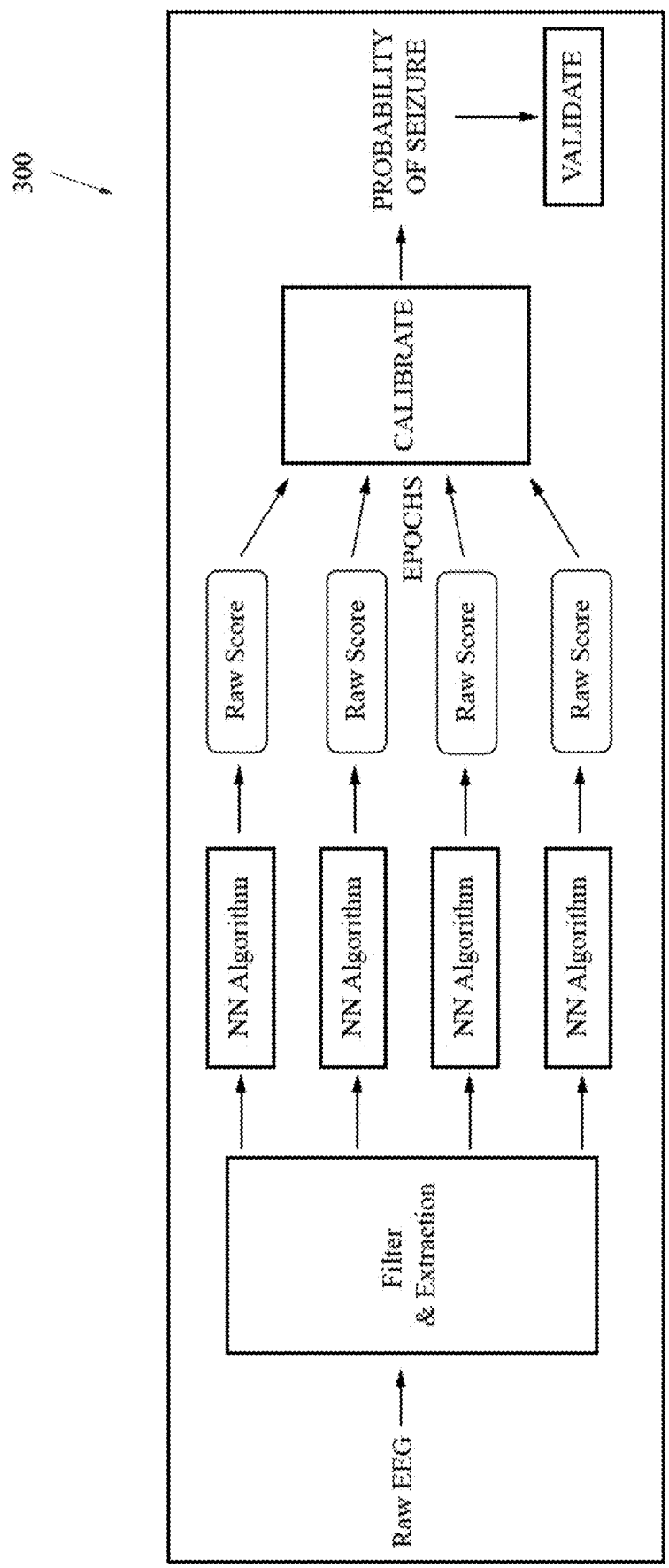
FIG. 3 is a block diagram for generating a probability value for a seizure.

FIG. 3 is a block diagram of a specific example of a system 300 for generating a probability value for detecting a seizure from a raw EEG recording. The raw EEG is processed through artifact reduction filters and neural network algorithms to generate raw score epochs that are calibrated to generate a probability value that a seizure is occurring. For example, taking one hundred epochs of one second duration that were given a 20% probability score of a seizure, the system determines if twenty of those one hundred were actually a seizure. This occurs by calibrating fifty of the epochs to measure if seizures occurred in ten of those fifty. The calibration will provide a probability value, which will be validated against the remaining fifty epochs. Next, one hundred epochs of one second duration that were given a 30% probability score of a seizure, the system determines if thirty of those one hundred were actually a seizure. This occurs by calibrating fifty of the epochs to measure if seizures occurred in fifteen of those fifty. The calibration will provide a probability value, which will be validated against the remaining fifty epochs. If fifteen of the remaining fifty evidence a seizure, then the probability value is validated. This also allows for training of a neural network to generate a validated probability value.

In another example, the digital input signals from the source 70 are a value for a fraudulent credit card transaction, a value for a monthly salary income for a loan applicant, a value for monthly rental income for a loan applicant, a value of a collateral for a loan, a value for a monthly car payment for a loan applicant, or a value of a number of years employed for a loan applicant.

Artificial neural networks (ANN) have been used to solve various tasks in numerous fields that are hard to solve using ordinary rule-based programming. An ANN can learn and adapt through learning algorithms. The types of ANNs and ANN architecture varies, mainly in the learning method.

The basic phases of an example algorithm 300 are shown in FIG. 3.

Figure 5:
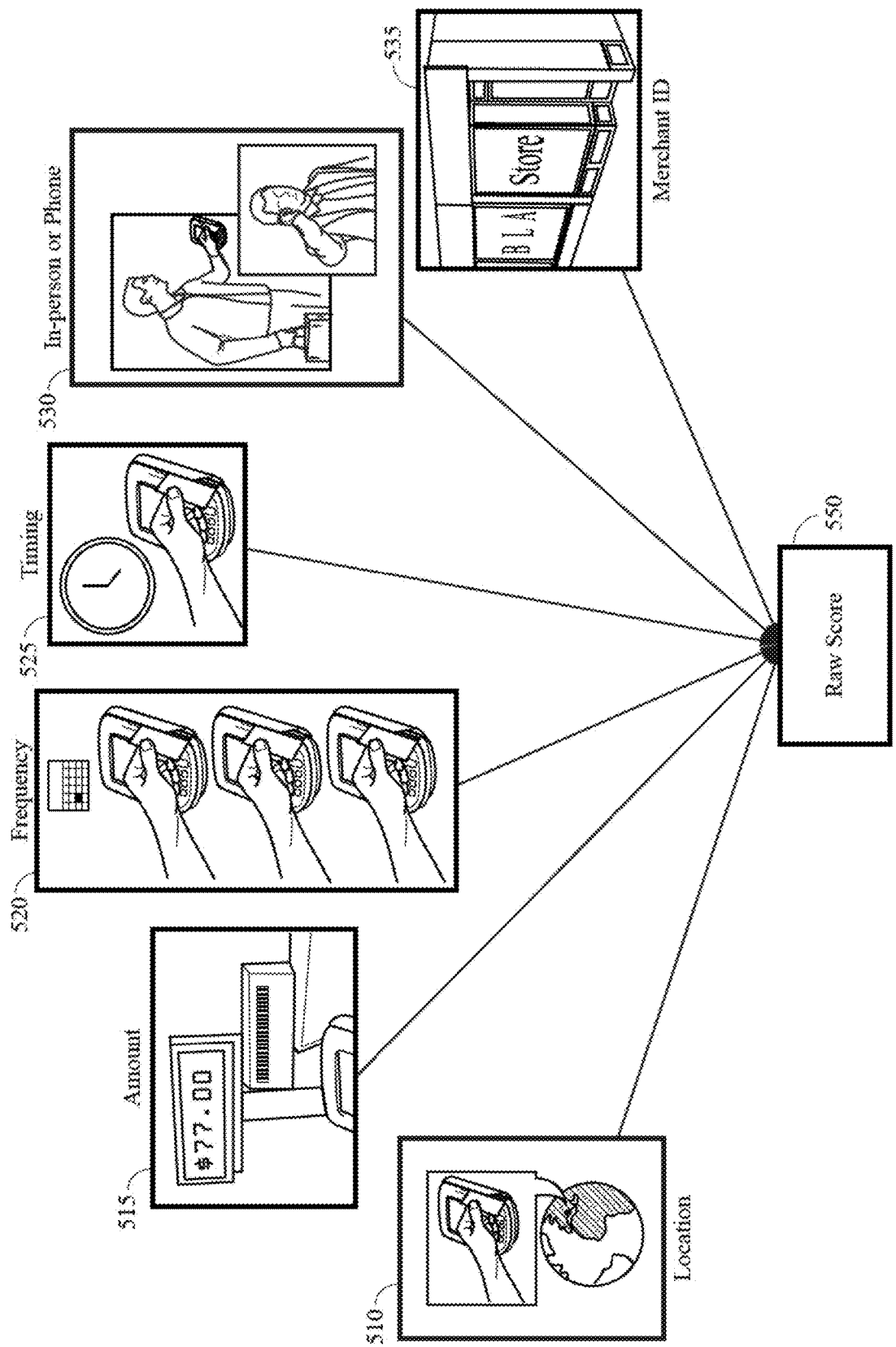
FIG. 5 is a block diagram of a flow chart of inputs for generating a raw score for a fraudulent credit card transaction.

A multilayer perceptron (MLP) is a feed forward ANN. FIG. 5 shows a graphical depiction of the MLP architecture with six inputs ($x_1$-$x_6$), three hidden nodes and a single output ($y_k$) Using a value for a fraudulent credit card transaction as the digital input signal as an example, an ANN can be used to recognize patterns of credit card use. The inputs can be information such as related to the cardholder or to the transactions. Example inputs can include types of purchases, frequency of specific purchases, time of purchase, or where purchases were made. The inputs are processed through the hidden node and then the output is a decision after processing. While the algorithm does not "match up" the pattern, the purpose is to determine the differences and find a threshold for the difference before determining that the use is fraudulent.

Figure 4:
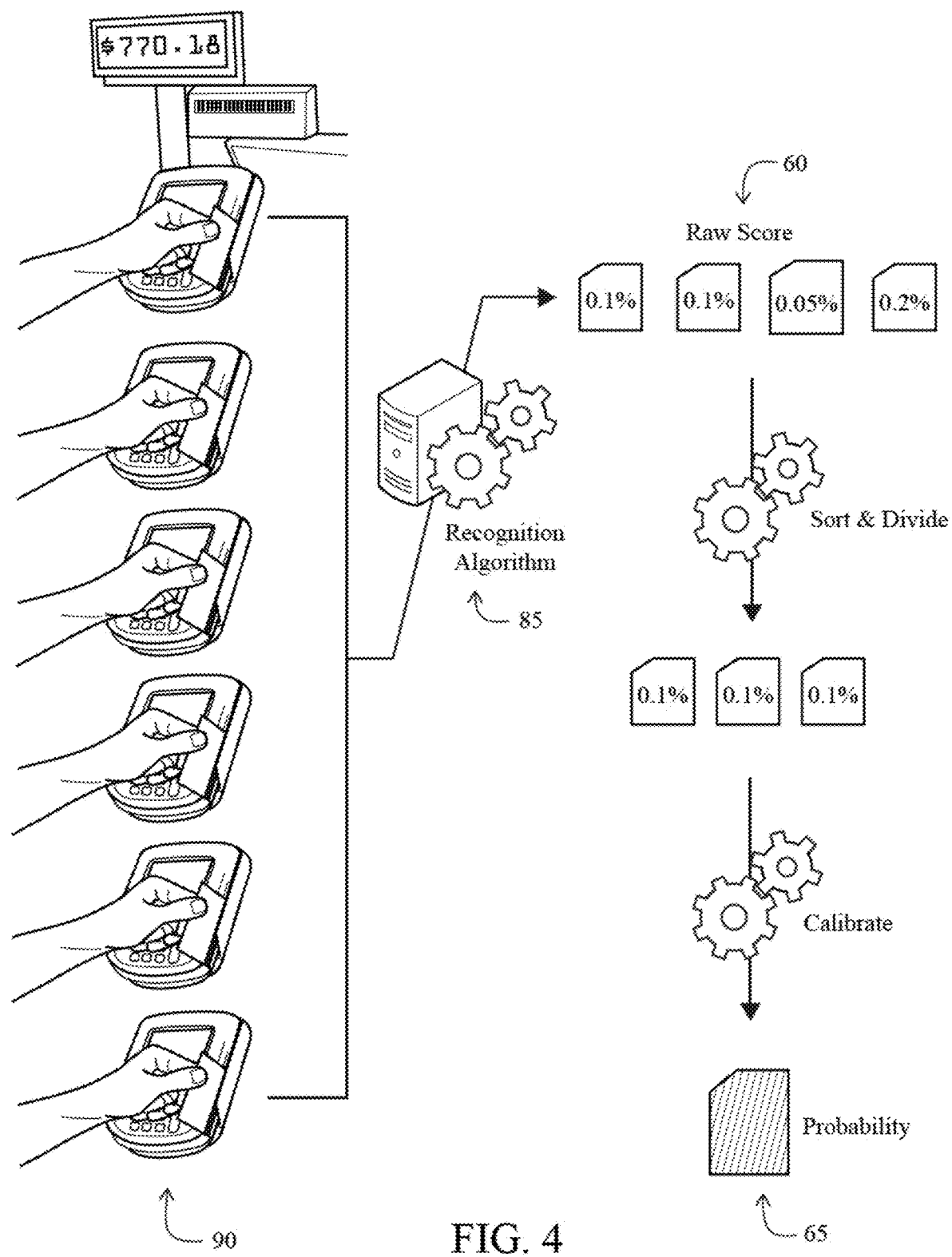
FIG. 4 is a block diagram of a flow chart of determining a probability value for a fraudulent credit card transaction.

FIGS. 4 and 5 are directed to an embodiment for determining a probability value for fraudulent credit card transactions. As shown in FIG. 4, at stage 510, multiple credit card transactions are performed credit card users. At stage 520, each transaction is transmitted to a server for a credit card company for authorization of each of the charges. The server utilizes an algorithm to generate a raw score value at stage 525. FIG. 5 illustrates some of the inputs utilized in an algorithm to generate a raw score value. The inputs for the algorithm of the example include: location 810, amount 815, frequency of credit card use 820, the timing of the use 830, in-person or by phone 840, and the identification of the merchant 850. These inputs are used to generate a raw score 800. However, those skilled in the pertinent art will recognize that other algorithms will use more or less inputs to generate a raw score without departing from the scope and spirit of the present invention.

Returning to FIG. 4, the raw scores are assorted by similar values, such as 0.1% for one group and 0.05% for another group. Then, half of the raw score values are calibrated to generate a probability value at 550. During the calibration stage, the groups sorted by raw scores are analyzed with the actual data for each credit card transaction in the group to calibrate the raw score value. For example, if all of the credit card transactions with a 0.1% raw score value area analyzed, then only 0.1% of the transactions should be fraudulent. However, if the actual data shows that the true value is 0.095% of the transactions were fraudulent, then the raw score value is calibrated and a probability value for those raw scores values is now 0.0095%.

Next, the other half of the raw scores values are validated with the corrected algorithm using the probability value. If the actual data for this second half of raw scores values demonstrates that the probability value is correct, then the calibrated algorithm has been validated. However, if the validation is incorrect, the process is repeated.

In classification, the task is to a classify a variable $y=x_0$ called class variable or output given a set of variables $x=x_1 \ldots x_n$, called attribute variables or input. A classifier $h:x \rightarrow y$ is a function that maps an instance of x to a value of y. The classifier is learned from a dataset d consisting of samples over (x, y). The learning task consists of finding an appropriate Bayesian network given a data set d over U. Let $U=\{x_1, \ldots, x_n\}$, $n \geq 1$ be a set of variables.

In an example for a loan application, there are two classes, low-risk and high-risk applicants. In order to find out if an applicant may default on the loan, a probability is calculated, P(Y|X), where X is the input, such as salary income, and Y is the 0 or 1 to indicate low-risk or high-risk, respectively. For a given X=x, P(Y=1|X=x)=0.9, the probability is 90 percent that the applicant is high-risk.

A perceptron models a biological neuron as a mathematical function, $$y = \sum_{j=1}^{d} w_j x_j + w_0$$

where the weighted sum, y, of the input values, $x_j \in \mathcal{R}$, $j=1, \ldots, d_j$, are calculated. The weights are $w_j \in \mathcal{R}$.

The following is a Perceptron Training Algorithm for training a MLP with K outputs.

```
For i = 1,..., K
    For j = 0,..., d
        w_ij ← rand(-0.01,0.01)
Repeat
    For all (x^t, r^t) ∈ X in random order
        For i = 1,..., K
            o_i ← 0
            For j = 0,..., d
                o_i ← o_i +w_ij x^t_j
        For i = 1,..., K
            y_i ← exp(o_i) / Σ_k exp(o_k)
        For i = 1,..., K
            For j = 0,..., d
                w_ij ← w_ij + η (r^t_i - y_i)x^t_j
```

Until convergence

Where η is the learning factor.

The following is a Backpropagation Algorithm for training a MLP with K outputs.

Initialize all $v_{ih}$ and $w_{hj}$ to rand(−0.01,0.01)

Repeat

For all $(x^t, r^t) \in X$ in random order

For h=1, . . . , H $z_h \leftarrow \text{sigmoid}(w^T_h x^t)$

For i=1, . . . , K $y_i = v^T_i z$

For i=1, . . . , K $\Delta v_i = \eta(r^t_i - y^t_i)z$

For h=1, . . . , H $\Delta w_h = \eta(\Sigma(r^t_i - y^t_i)v_{ih})z_h(1-z_h)x^t$ For i=1, . . . , K $v_i \leftarrow v_i + \Delta v_i$ For h=1, . . . , H $w_h \leftarrow w_h + \Delta w_h$ until convergence.

Figure 6:
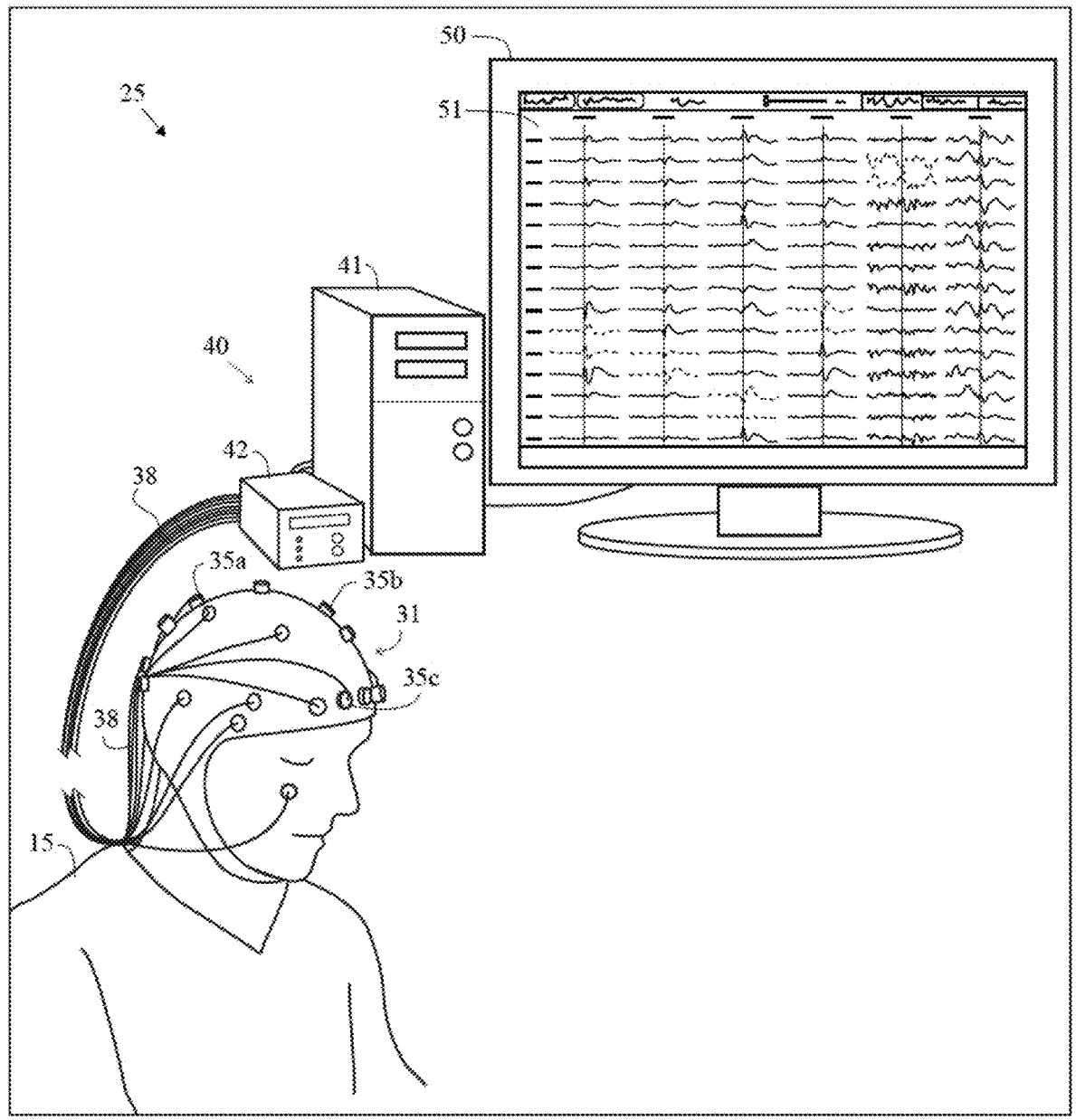
FIG. 6 is an illustration of an EEG system used on a patient.

FIG. 6 illustrates a system 25 for a user interface for automated artifact filtering for an EEG. A patient 15 wears an electrode cap 31, consisting of a plurality of electrodes 35a-35c, attached to the patient's head with wires 38 from the electrodes connected to an EEG machine component 40 which consists of an amplifier 42 for amplifying the signal to a computer 41 with a processor, which is used to analyze the signals from the electrodes 35 and create an EEG recording 51, which can be viewed on a display 50. A button on computer 41, either through a keyboard or touchscreen button on display 50 allows for the application of a plurality of filters to remove the plurality of artifacts from the EEG and generate a clean EEG. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording, a raw score. The processor 41 is also configured to calibrate the raw score to generate a probability value that an event has occurred and then to generate a display of the probability value versus time. Further, the processor 41 is configured to validate the probability value. The processor is also connected to the display for displaying a final output.

The EEG is optimized for automated artifact filtering. The EEG recordings are then processed using neural network algorithms to generate a processed EEG recording which is analyzed for display.

An additional description of analyzing EEG recordings is set forth in Wilson et al., U.S. patent application Ser. No. 13/620,855, filed on Sep. 15, 2012, for a Method And System For Analyzing An EEG Recording, which is hereby incorporated by reference in its entirety.

Figure 7:
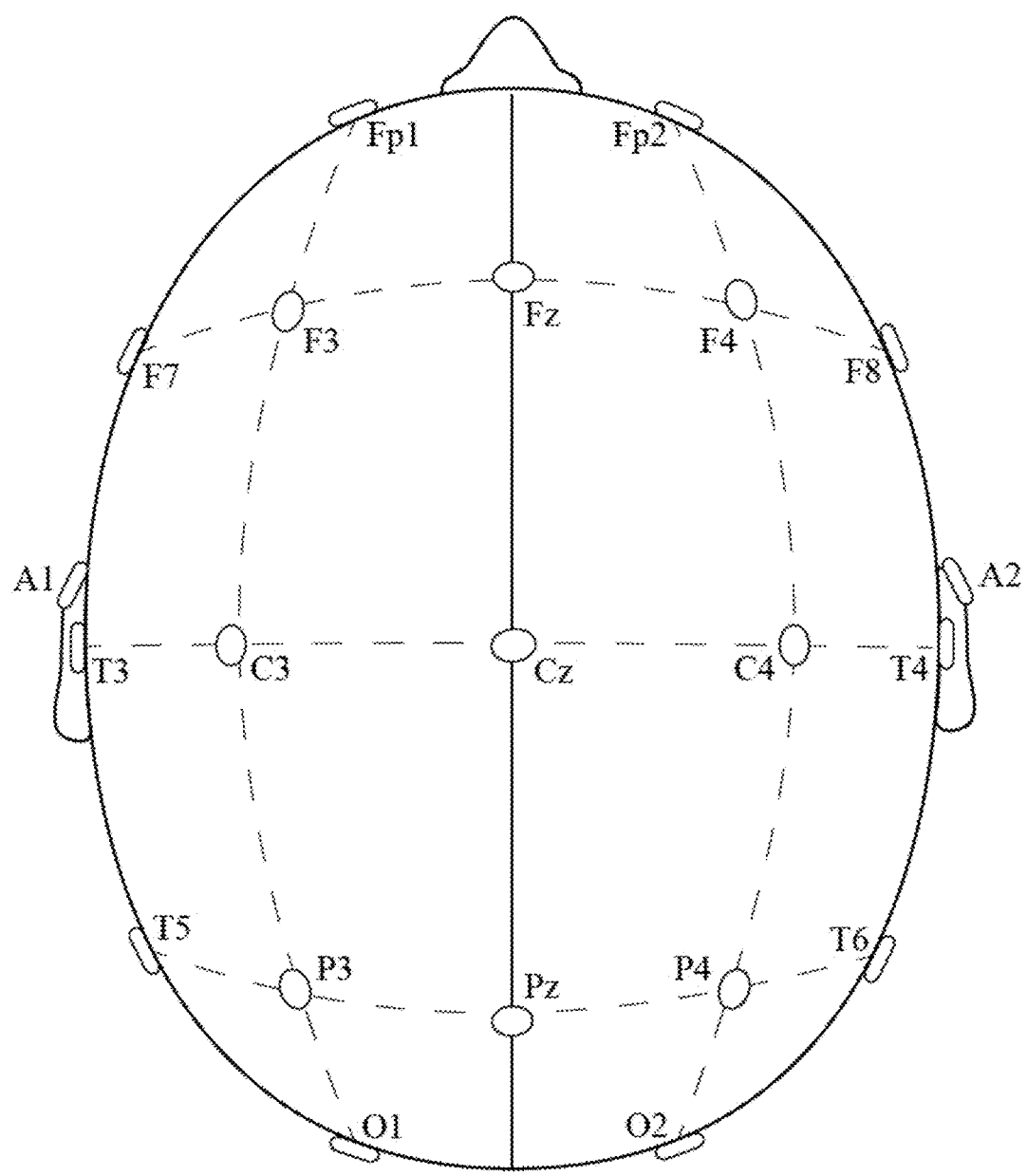
FIG. 7 is a map representing the international 10-20 electrode system for electrode placement for an EEG.
Figure 8:
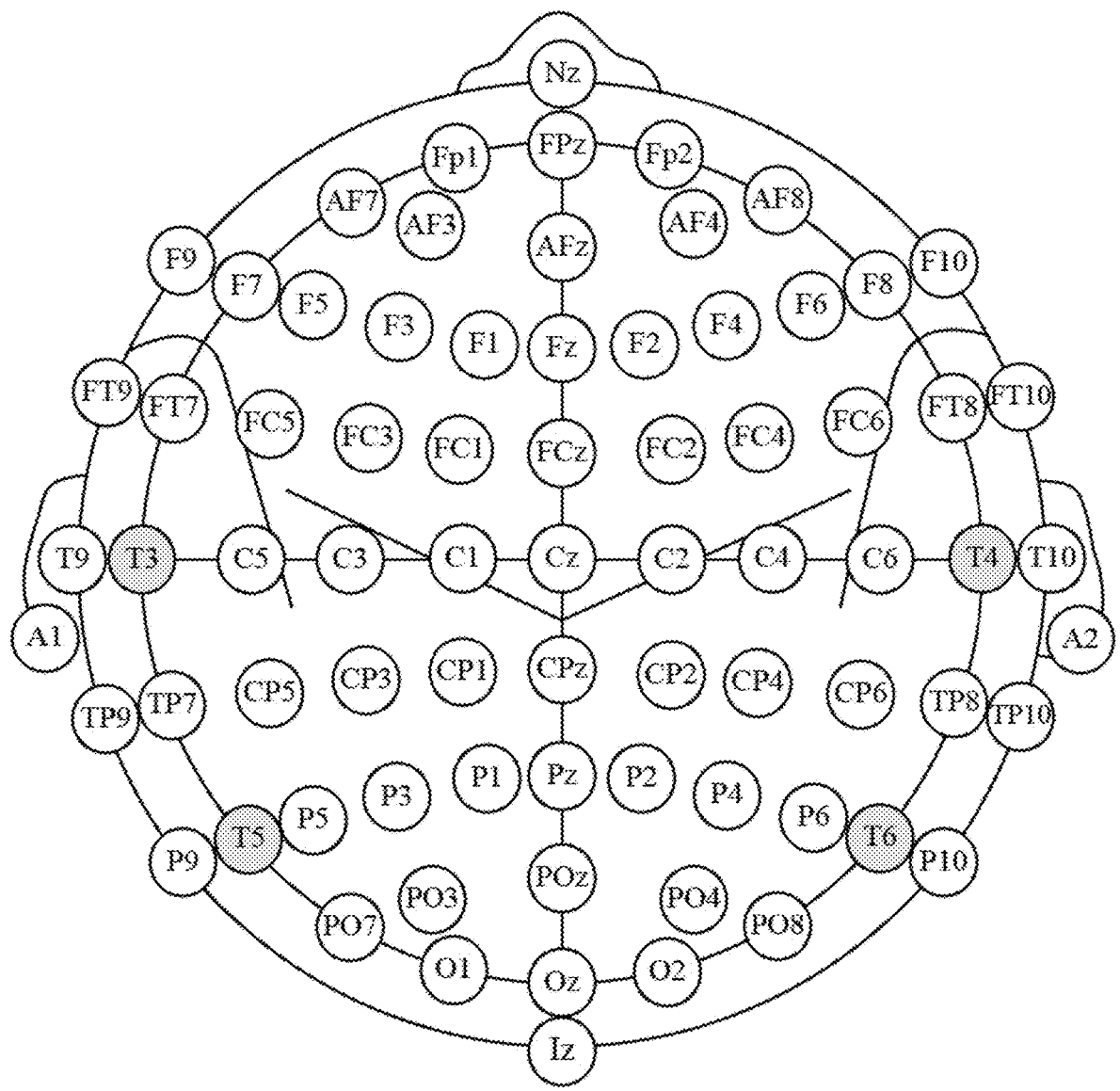
FIG. 8 is a detailed map representing the intermediate 10% electrode positions, as standardized by the American Electroencephalographic Society, for electrode placement for an EEG.

A patient has a plurality of electrodes attached to the patient's head with wires from the electrodes connected to an amplifier for amplifying the signal to a processor, which is used to analyze the signals from the electrodes and create an EEG recording. The brain produces different signals at different points on a patient's head. Multiple electrodes are positioned on a patient's head. The CZ site is in the center. The number of electrodes determines the number of channels for an EEG. A greater number of channels produce a more detailed representation of a patient's brain activity. Preferably, each amplifier 42 of an EEG machine component 40 corresponds to two electrodes 35 attached to a head of the patient 15. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. FIG. 7 is a map representing the international 10-20 electrode system for electrode placement for an EEG. FIG. 8 is a detailed map representing the intermediate 10% electrode positions, as standardized by the American Electroencephalographic Society, for electrode placement for an EEG. A more thorough description of an electrode utilized with the present invention is detailed in Wilson et al., U.S. Pat. No. 8,112,141 for a Method And Device For Quick Press On EEG Electrode, which is hereby incorporated by reference in its entirety.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources."

In one example an algorithm called BSS-CCA is used to remove the effects of muscle activity from the EEG. Using the algorithm on the recorded montage will frequently not produce optimal results. In this case it is generally optimal to use a montage where the reference electrode is one of the vertex electrodes such as CZ in the international 10-20 standard. In this algorithm the recorded montage would first be transformed into a CZ reference montage prior to artifact removal. In the event that the signal at CZ indicates that it is not the best choice then the algorithm would go down a list of possible reference electrodes in order to find one that is suitable.

An additional description of analyzing EEG recordings is set forth in Wilson et al., U.S. patent application Ser. No. 13/684,469, filed on Nov. 23, 2012, for a User Interface For Artifact Removal In An EEG, which is hereby incorporated by reference in its entirety. An additional description of analyzing EEG recordings is set forth in Wilson et al., U.S. patent application Ser. No. 13/684,556, filed on Nov. 25, 2012, for a Method And System For Detecting And Removing EEG Artifacts, which is hereby incorporated by reference in its entirety.

FIGS. 9, 9A, 9B and 9C illustrate a graphical display of the amount of artifact present in an EEG recording. An artifact intensity channel 110 is shown as a series of horizontal lines 111. The plurality of horizontal lines 111 shown comprises a horizontal line 112 for a muscle artifact, a horizontal line 113 for a chewing artifact, a horizontal line 114 for a vertical eye movement artifact, and a horizontal line 115 for a lateral eye movement artifact. Those skilled in the pertinent art will recognize that more or less horizontal lines may be used without departing from the scope and spirit of the present invention.

Figure 9:
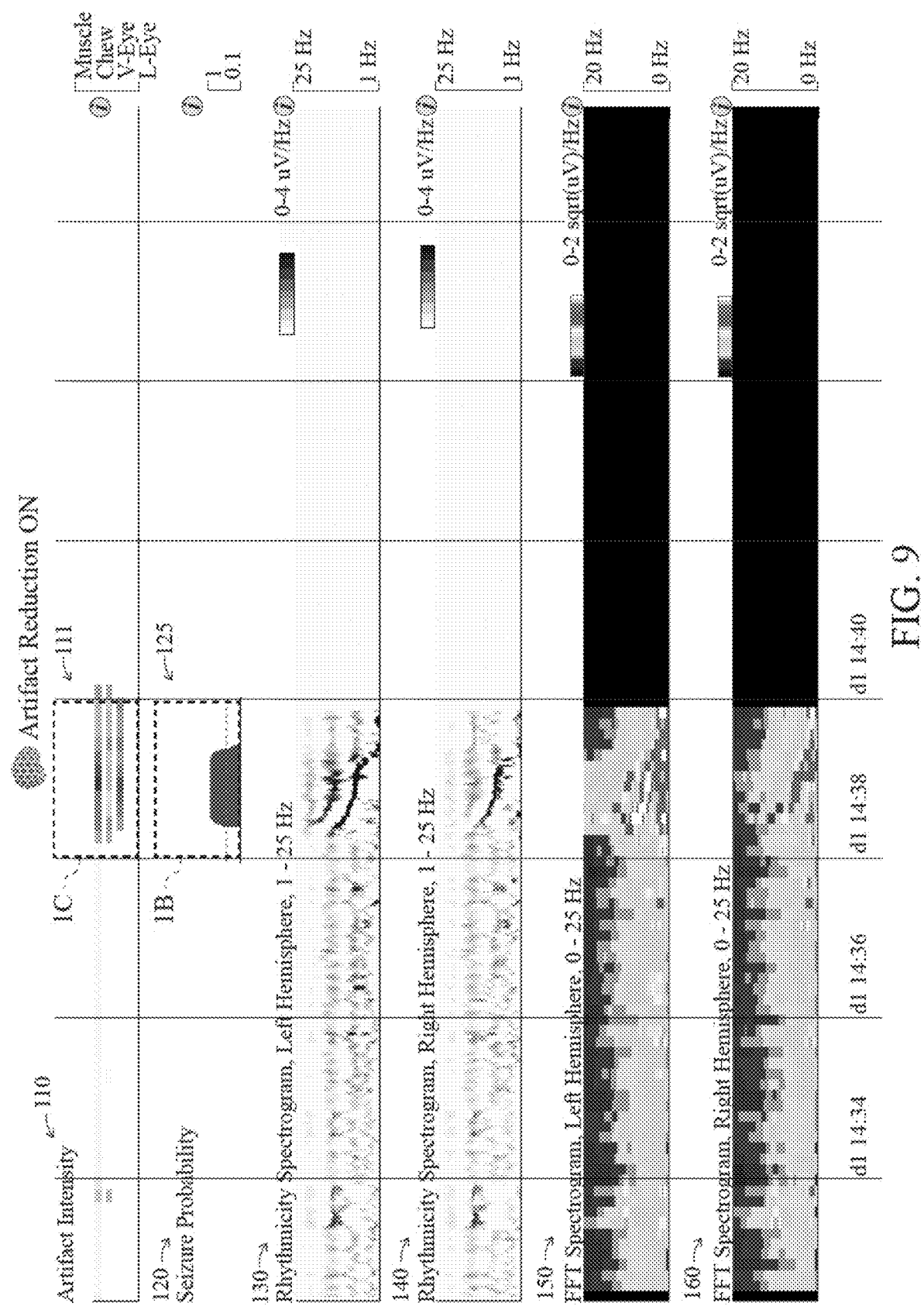
FIG. 9 is a graphical display of the amount of artifact present in an EEG recording.
Figure 9A:
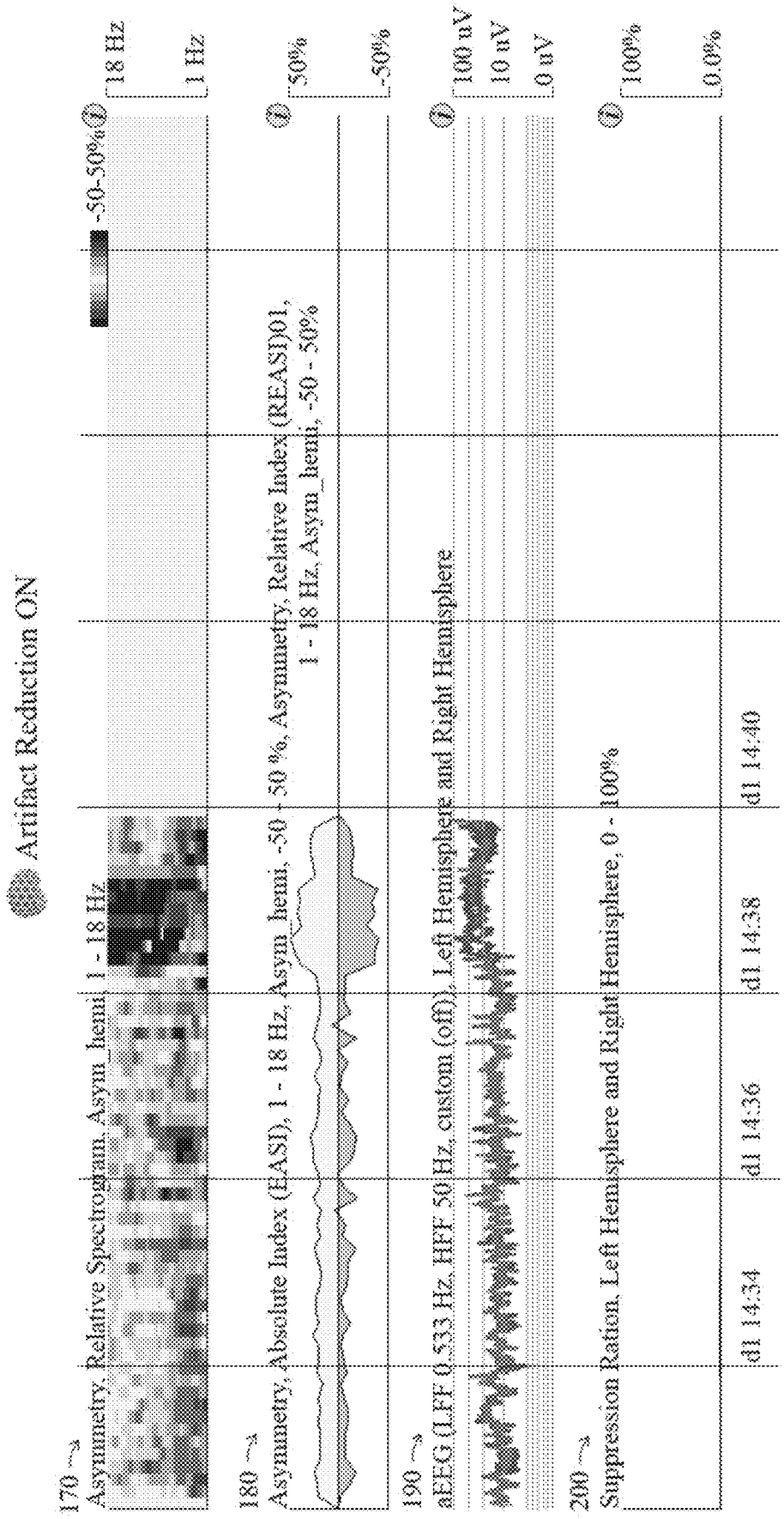
FIG. 9A is a graphical display of the amount of artifact present in an EEG recording.
Figure 9B:
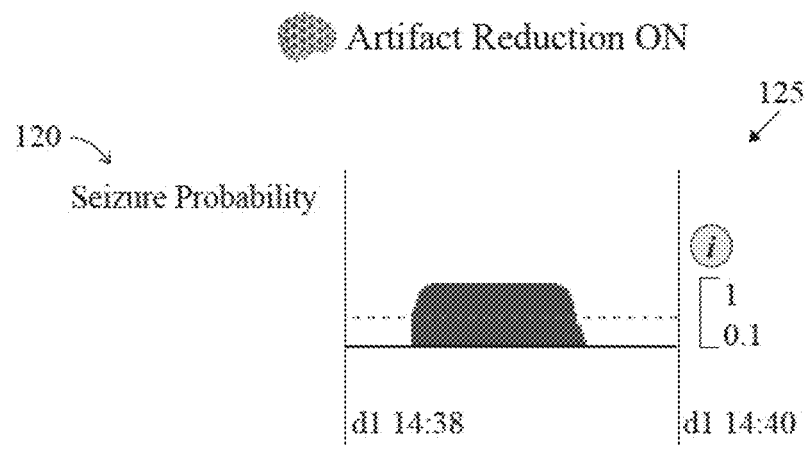
FIG. 9B is an enlarged and isolated view of a box 1B of a seizure probability channel of FIG. 9.
Figure 9C:
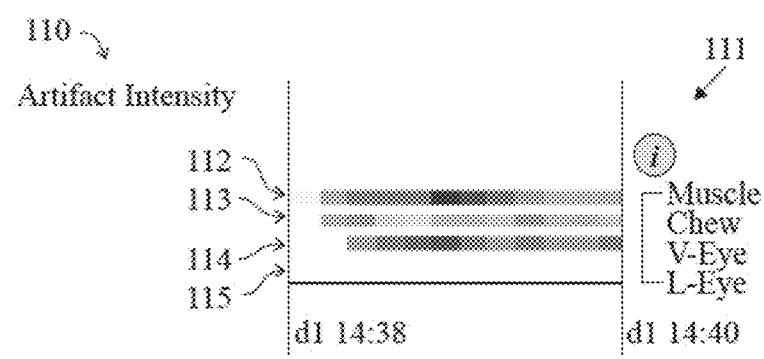
FIG. 9C is an enlarged and isolated view of horizontal lines of the artifact intensity channel of FIG. 9.

Also shown in FIGS. 9 and 9A are a seizure probability channel 120, a rhythmicity spectrogram, left hemisphere channel 130, a rhythmicity spectrogram, right hemisphere channel 140, a FFT spectrogram left hemisphere channel 150, a FFT spectrogram right hemisphere channel 160, an asymmetry relative spectrogram channel 170, a asymmetry absolute index channel 180, an aEEG channel 190, and a suppression ration, left hemisphere and right hemisphere channel 200.

Rhythmicity spectrograms allow one to see the evolution of seizures in a single image. The rhythmicity spectrogram measures the amount of rhythmicity which is present at each frequency in an EEG record.

The seizure probability trend shows a calculated probability of seizure activity over time. The seizure probability trend shows the duration of detected seizures, and also suggests areas of the record that may fall below the seizure detection cutoff, but are still of interest for review. The seizure probability trend when displayed along with other trends, provides a comprehensive view of quantitative changes in an EEG.

Figure 12:
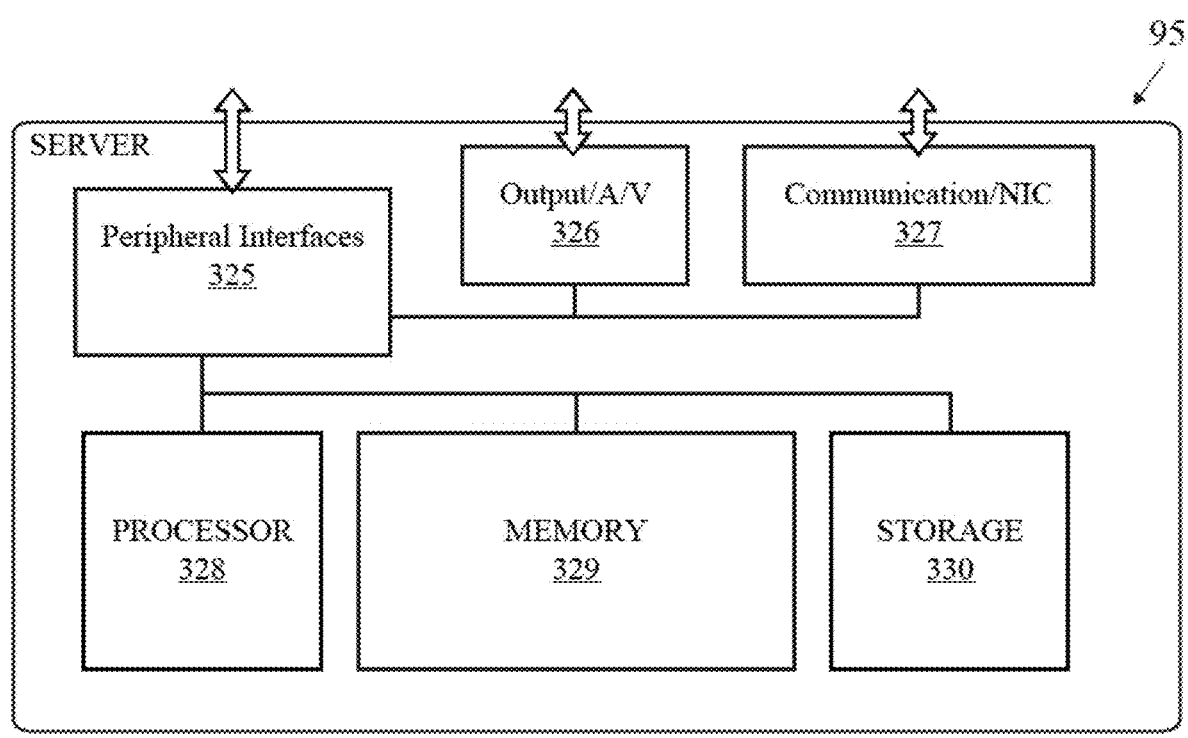
FIG. 12 is a block diagram of a computing device for EEG processing.

As shown in FIG. 12, the EEG machine component 95 preferably is a computer that includes peripheral interfaces 325, an output/A/V 326, a communication/NIC 327, a processor 328, a memory 329, and a storage 330. Those skilled in the pertinent art will recognize that the machine component 95 may include other components without departing from the scope and spirit of the present invention.

A patient has a plurality of electrodes attached to the patient's head with wires from the electrodes connected to an amplifier for amplifying the signal to a processor, which is used to analyze the signals from the electrodes and create an EEG recording. The brain produces different signals at different points on a patient's head. Multiple electrodes are positioned on a patient's head as shown in FIGS. 7 and 8. The number of electrodes determines the number of channels for an EEG. A greater number of channels produce a more detailed representation of a patient's brain activity. Preferably, each amplifier 42 of an EEG machine component 40 corresponds to two electrodes 35 attached to a patient's 15 head. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording, which is analyzed for display.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources." The sources that are judged as containing artifact are removed and the rest of the sources are reassembled into the channel set.

Figure 10:
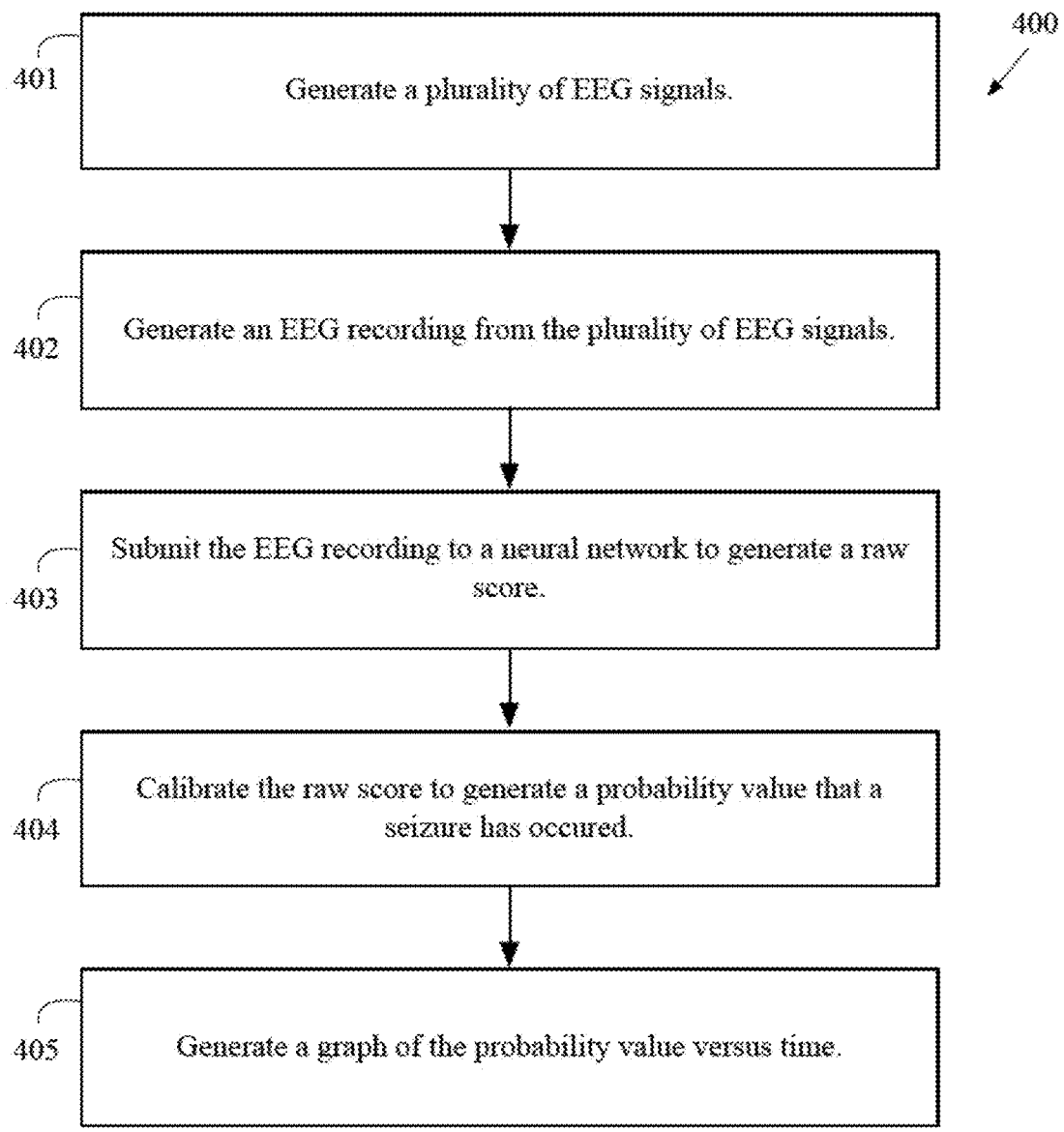
FIG. 10 is a flow chart of a method for generating a probability value for a seizure.

FIG. 10 shows a flow chart for a method, generally designated 400, of the present invention. A method 400 for validating a seizure probability for an EEG starts at step 401, generating a plurality a plurality of EEG signals. Step 402 is generating an EEG recording from the plurality of EEG signals. Step 403 is submitting the EEG recording to a neural network to generate a raw score. Step 404 is calibrating the raw score to generate a probability value that a seizure has occurred. Step 405 is generating a graph of the probability value versus time. The method 400 further includes validating the probability value (not shown).

Figure 11:
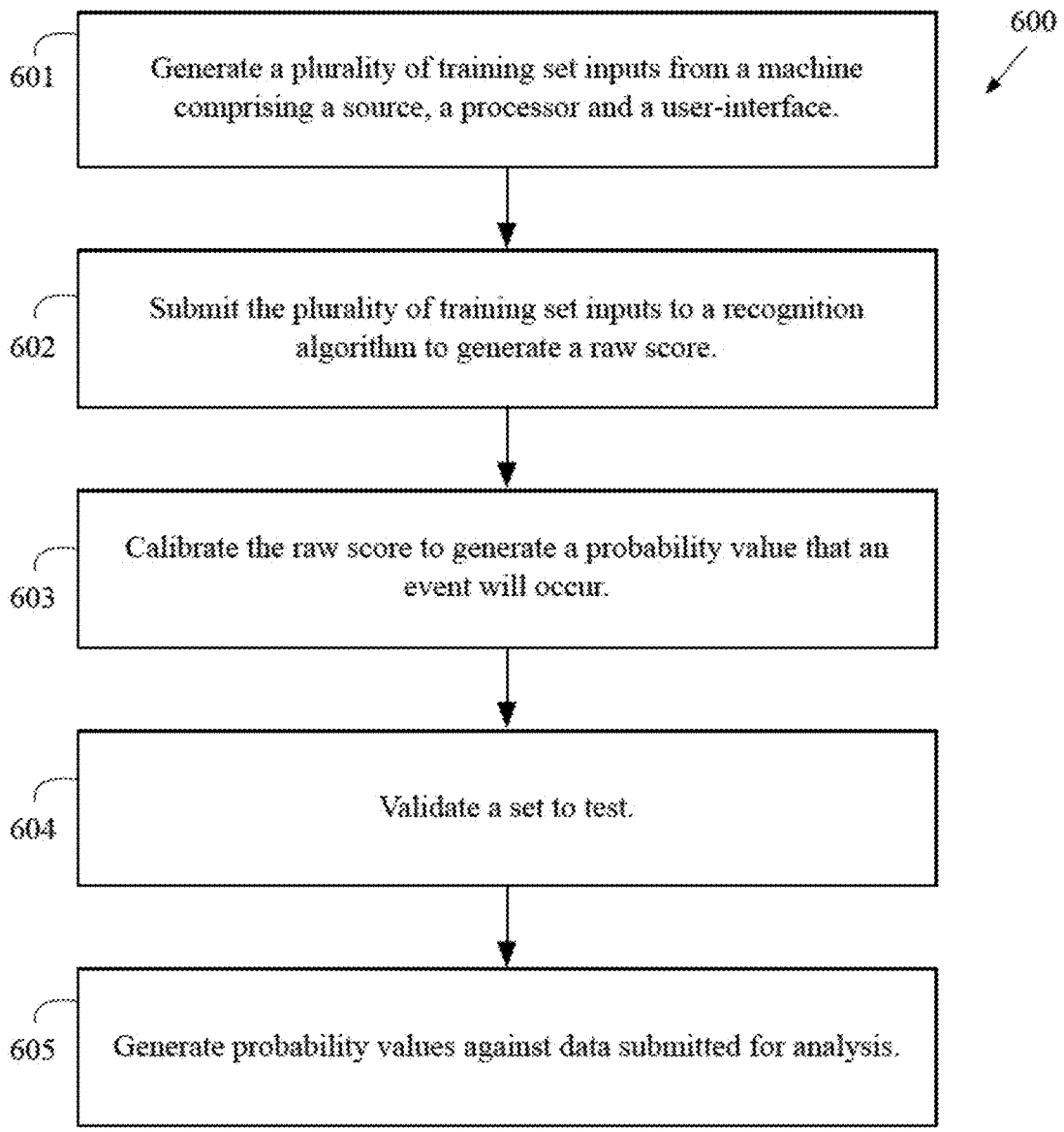
FIG. 11 is a flow chart of a method for validating a probability value for an event.

FIG. 11 shows a flow chart for a method, generally designated 600, of the present invention. A method 600 for generating a probability value for an event starts at block 601 where multiple training set inputs are generated from a machine comprising a source, a processor and a user-interface. At block 602, the multiple training set inputs are submitted to a recognition algorithm to generate a raw score. At block 603, the raw score is calibrated to generate a probability value that an event will occur. At block 604, a set is validated to test that the probability value is correct. At block 605, the probability values are generated against data submitted for analysis.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A non-transitory computer-readable medium that stores a program that causes a processor to perform functions to generate a probability value for an event by executing the following steps:
   receiving a plurality of input signals at a first processor, plurality of input signals generated from a source;
   submitting the plurality of input signals to a multilayer perceptron operating on a first processor to generate a plurality of raw scores;
   sorting at the first processor the plurality of raw scores by similar values;
   calibrating at the first processor a first half of the plurality of raw scores with similar values to generate a probability value that an event will occur;
   validating at the first processor the probability value that the event has occurred with actual data;
   validating at the first processor a second half of the plurality of raw scores with similar values at the multilayer perceptron to determine if the probability value is correct; and,
   generating at the first processor a graph of the probability value versus time on a graphical display;
   wherein the plurality of digital input signals comprises at least one of a value for a fraudulent credit card transaction, a value for a monthly salary income for the loan applicant, a value for monthly rental income for the loan applicant, a value of a collateral for the loan, a value for a monthly car payment for the loan applicant, or a value of a number of years employed for the loan applicant.

2. The non-transitory computer-readable medium according to claim 1 wherein the multilayer perceptron comprises a plurality of inputs, a plurality of hidden nodes and a single output.

3. A system for generating a probability value for an event, the system comprising:
   a source for generating a plurality of digital input signals;
   a processor connected to the source to receive from the plurality of digital input signals from the source; and
   a graphical display connected to the processor for displaying a final output;
   wherein the plurality of digital input signals is submitted to a multilayer perceptron at the processor to generate a plurality of raw scores;
   wherein the processor is configured to sort the plurality of raw scores by similar values;
   wherein the processor is configured to calibrate a first half of the plurality of raw scores to generate a probability value that an event has occurred;
   wherein the processor is configured to validate the probability value that an event has occurred with actual data of an event;
   wherein the processor is configured to validate a second half of the plurality of raw scores with similar values from the multilayer perceptron to determine if the probability value is correct;
   wherein the processor is configured to generate a display of the probability value versus time on the graphical display;
   wherein the plurality of digital input signals comprises at least one of a value for a fraudulent credit card transaction, a value for a monthly salary income for the loan applicant, a value for monthly rental income for the loan applicant, a value of a collateral for the loan, a value for a monthly car payment for the loan applicant, or a value of a number of years employed for the loan applicant.

4. The system according to claim 3 wherein the multilayer perceptron consist essentially of a plurality of inputs, a plurality of hidden nodes and a single output.

5. A non-transitory computer-readable medium that stores a program that causes a processor to perform functions to determine a probability value for an event by executing the following steps:
   generating a plurality of training set inputs from a machine comprising a source, a processor and a user-interface;
   submitting the plurality of training set inputs to a recognition algorithm to generate a raw score;
   calibrating the raw score to generate a probability value that an event will occur;
   validating a set to test; and
   generating probability values against data submitted for analysis.

* * * * *